(12) United States Patent
Evans

(10) Patent No.: US 9,174,005 B2
(45) Date of Patent: Nov. 3, 2015

(54) INJECTION DEVICE

(75) Inventor: Timothy Simon Evans, Oxford (GB)

(73) Assignee: OWEN MUMFORD LIMITED, Oxford (GB)

( * ) Notice: Subject to any disclaimer, the term of this patent is extended or adjusted under 35 U.S.C. 154(b) by 225 days.

(21) Appl. No.: 12/300,220

(22) PCT Filed: May 10, 2007

(86) PCT No.: PCT/GB2007/001724
§ 371 (c)(1),
(2), (4) Date: Dec. 9, 2008

(87) PCT Pub. No.: WO2007/129106
PCT Pub. Date: Nov. 15, 2007

(65) Prior Publication Data
US 2009/0124981 A1 May 14, 2009

(30) Foreign Application Priority Data
May 10, 2006 (GB) .................................. 0609229.0

(51) Int. Cl.
A61M 5/32 (2006.01)
A61M 5/20 (2006.01)
A61M 5/31 (2006.01)

(52) U.S. Cl.
CPC ........... *A61M 5/3202* (2013.01); *A61M 5/2033* (2013.01); *A61M 5/3129* (2013.01);
(Continued)

(58) Field of Classification Search
CPC ..... A61M 5/2033; A61M 5/20; A61M 5/326; A61M 2005/3247; A61M 5/24; A61M 2005/206; A61M 5/3202; A61M 2005/2073; A61M 2205/583; A61M 2005/3267; A61M 2005/202; A61M 5/3213; A61M 5/3257; A61M 15/0025; A61M 5/3232; A61M 2005/147573; A61M 5/1456; A61M 5/50; A61M 5/5086; A61M 2005/2481
USPC ............. 604/131–139, 110, 68–72, 192–198, 604/263
See application file for complete search history.

(56) References Cited

U.S. PATENT DOCUMENTS 3,702,609 A * 11/1972 Steiner ........................... 604/139
5,312,366 A * 5/1994 Vailancourt ................... 604/192
(Continued)

FOREIGN PATENT DOCUMENTS

GB 2 414 398 11/2005
JP 61-051828 U 4/1986
(Continued)

OTHER PUBLICATIONS

International Search Report dated Dec. 19, 2007, from corresponding PCT application.
(Continued)

*Primary Examiner* — Shisma Mehta
*Assistant Examiner* — Brandy S Lee
(74) *Attorney, Agent, or Firm* — Young & Thompson

(57) ABSTRACT

An injection device comprises a housing ($10_1$) to ($10_4$) containing a syringe (24). The contents of the syringe (24) are viewable through a window (14) in the mid-section ($10_2$) of the housing. The window (14) is concealed by a slideable shutter (12). The slideable shutter (12) is biased by a bias spring (22) which also biases an internal syringe carrier. Also disclosed is a reversible needle cap which operates initially to cap the front end of the housing and, upon removal thereof, pulls a needle sheath (30) off the syringe needle (26). The cap is designed to be reversible so that, after use, it can be reversed and reconnected to the housing to cover the exposed needle.

14 Claims, 3 Drawing Sheets

(52) U.S. Cl.
CPC ............ *A61M5/3204* (2013.01); *A61M 5/3213* (2013.01); *A61M 5/3243* (2013.01); *A61M 2005/206* (2013.01); *A61M 2005/2073* (2013.01); *A61M 2005/3103* (2013.01); *A61M 2005/3125* (2013.10)

(56) References Cited

U.S. PATENT DOCUMENTS

| | | | |
|---|---|---|---|
| 6,086,569 A * | 7/2000 | Schweizer | 604/227 |
| 6,530,904 B1 | 3/2003 | Edwards et al. | |
| 6,752,798 B2 * | 6/2004 | McWethy et al. | 604/506 |
| 2002/0050462 A1 | 5/2002 | Penney et al. | |
| 2004/0230153 A1 * | 11/2004 | Demay et al. | 604/6.15 |
| 2005/0027255 A1 * | 2/2005 | Lavi et al. | 604/135 |
| 2005/0124933 A1 * | 6/2005 | Segal | 604/110 |
| 2005/0148933 A1 | 7/2005 | Raven et al. | |
| 2008/0228143 A1 * | 9/2008 | Stamp | 604/157 |
| 2009/0088787 A1 | 4/2009 | Koike et al. | |

FOREIGN PATENT DOCUMENTS

| | | | |
|---|---|---|---|
| JP | 2-005972 A | 1/1990 | |
| JP | 7-002238 U | 1/1995 | |
| JP | 2003-088586 A | 3/2003 | |
| JP | 2003-093510 A | 4/2003 | |
| JP | 2003-327212 A | 11/2003 | |
| WO | 03005907 A1 | 1/2003 | |
| WO | 03/013632 | 2/2003 | |
| WO | 2005/070481 | 8/2005 | |
| WO | 2006/061170 | 6/2006 | |
| WO | WO2006061170 * | 6/2006 | A61M 5/31 |

OTHER PUBLICATIONS

Japanese Office Action, dated Jan. 24, 2012, from corresponding Japanese application.

Japanese Office Action dated Aug. 21, 2012, from corresponding JP application.

* cited by examiner

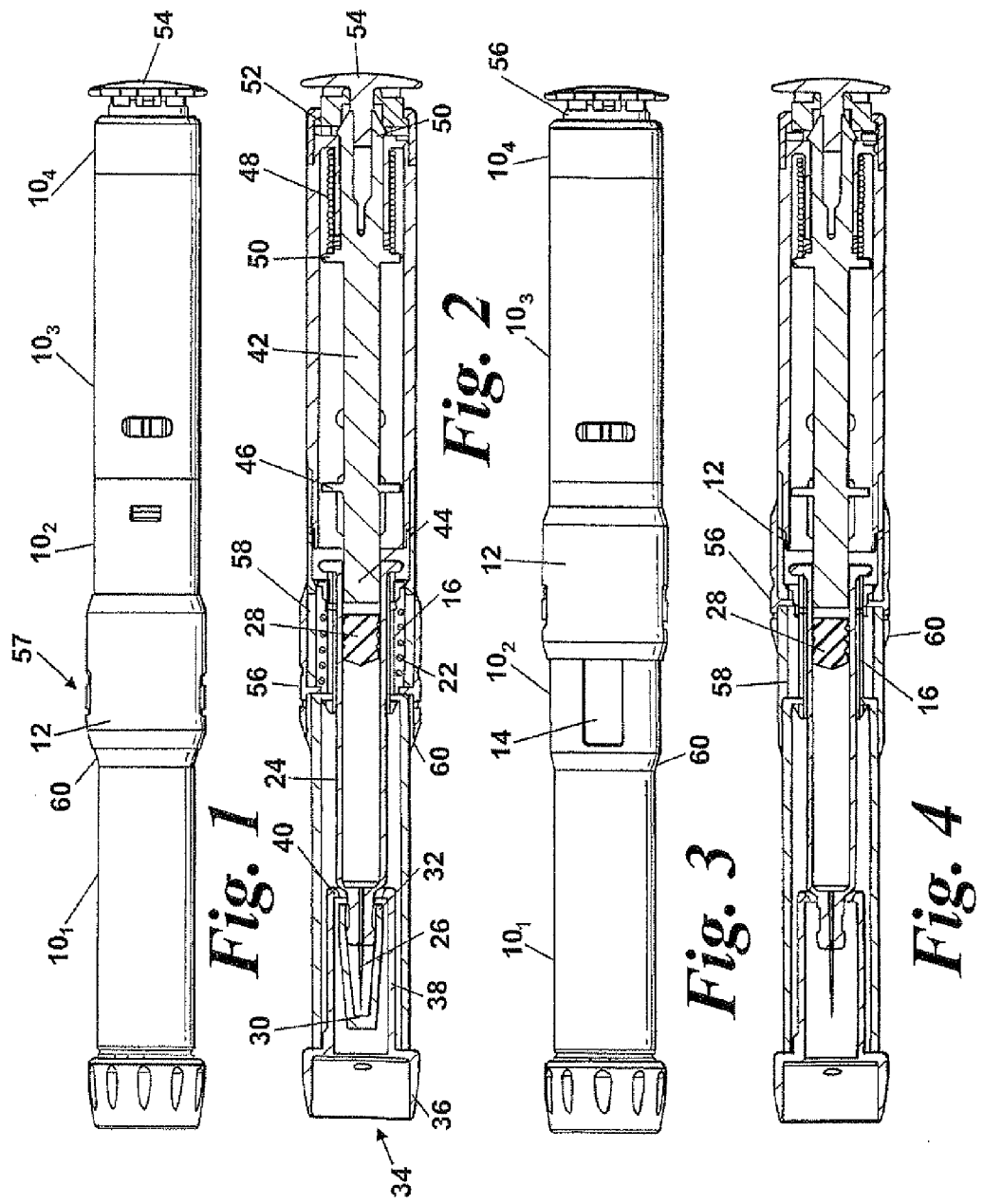

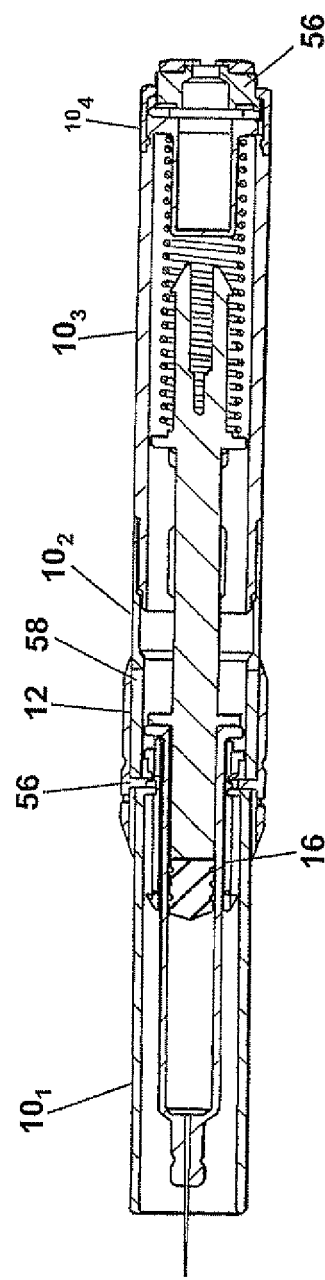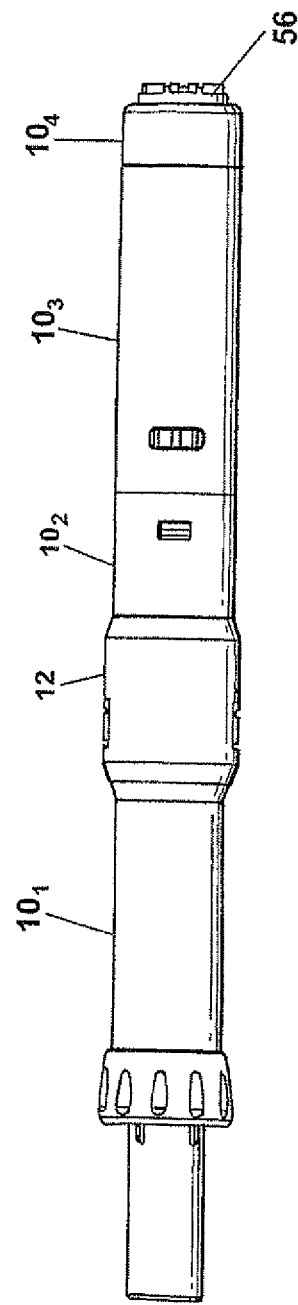
Fig. 6
Fig. 7

INJECTION DEVICE

This invention relates to injection devices of the type comprising a housing which contains a syringe or cartridge which contains a therapeutic substance for injection into the human or animal body.

BACKGROUND OF THE INVENTION

Certain therapeutic substances, such as for example adrenaline, can be degraded by prolonged exposure to light with a result that their therapeutic effect is diminished or lost. Previously this has been overcome by disposing the syringe or cartridge in a housing which is opaque to at least the primary waveband of light responsible for the degradation. Alternatively, the device has itself been stored within an outer container which provides a tight shielding or filtering effect. However, the requirement to shield the substance from the light is in direct conflict with a requirement that the user be able to inspect the state of the therapeutic substance within the syringe before making the injection to check that it has not discoloured or leaked out. In the first type of injection device this is not possible and, in the second, it is possible but only at the expense of having to provide a separate outer container.

SUMMARY OF THE INVENTION

Accordingly, in one aspect of this invention, there is provided an injection device comprising:

an elongate housing for receiving a syringe or cartridge in use, the housing having a forward end and a rearward end and a window or viewing aperture through which the contents of the syringe or cartridge may be inspected;

a shutter element moveable between a revealing position in which said window or viewing aperture is visible, and a concealing position in which said window or viewing aperture is concealed, and bias means biasing said shutter element towards its concealing position.

In this manner, the contents of the syringe or cartridge may be readily viewed by retracting the shutter element to view the contents through the window. Provision of a movable shutter element on the housing itself means that no separate outer container is required and the device is ready for use in an emergency. The device includes bias means biasing said shutter element towards its concealing position, so that on release of the shutter element from a retracted position, the bias means returns the shutter element to its concealing position.

Preferably, the shutter element comprises a sleeve element generally surrounding said housing and slideable with respect thereto. The sliding movement is preferably longitudinal although rotational sliding movement is not excluded.

The bias means may conveniently comprise a spring, such as for example a coil spring arranged generally concentrically with in the housing.

In one arrangement, where the shutter element is moveable longitudinally with respect to the housing, the housing may comprise at least one elongate slot adjacent said bias means or spring, and the shutter element may include an inwardly projecting portion adapted to project inwardly through said slot to engage said spring. There may be two such slots disposed one to each side of the housing with the shutter element including two respective projecting portions.

For ease of assembly of the device, the or each inwardly projecting portion on the shutter element is preferably resiliently flexible to allow the shutter element to be eased over the exterior of the housing during assembly.

In a particularly preferred arrangement, where the housing includes a carrier for receiving in use said syringe or cartridge, and the carrier is mounted for generally longitudinal movement between a forward and rearward position, the bias means that biases the shutter element also biases said carrier. This is particularly advantageous as using the same bias means reduces the component count and means that the diameter of the device does not have to be enlarged to accommodate two separate springs.

Preferably, the carrier includes an elongate slot, and an inwardly projecting portion on the housing cooperates with said slot to limit longitudinal movement thereof. The elongate slot on the housing may conveniently be generally aligned with the elongate slot on the carrier, with the inward projection on the housing disposed at one end of the housing slot.

Also, in many cases, on completion of an injection the carrier is held in its forward position by the force of the drive spring, overcoming the force of the bias means. This means that opening movement of the shutter element is prevented or restricted by the carrier being in its forward position, thereby providing an external indication that the device has been used.

In one arrangement, the syringe or cartridge housed in use inside said housing has a needle which is initially protected by a longitudinally removable sheath, and the injection device further includes a removable cap for being fitted to the forward end of the housing to close said end for storage, said cap having a rearwardly extending element adapted to engage at its rearward end behind a base of the removable sheath whereby, in use, on removal of said cap from the forward end of said housing, said sheath is pulled off said needle by the engagement with said rearwardly extending element.

The rearwardly extending element may be conveniently of generally hollow cylindrical form, with the rearward end thereof including an inwardly directed rib or tooth for engaging behind the base of said sheath. The engagement between the rearwardly extending element and the base of said sheath is preferably resilient whereby the rearward end of said rearwardly extending element may move resiliently past the base of the needle sheath to a position ready to capture the sheath on removal of said cap.

Preferably, said cap is reversible, whereby, following use of said device, the cap may be refitted in reverse configuration with said rearwardly extending element extending forwardly to shroud said needle. This is particularly advantageous as it provides the device with a safety shroud for post-use.

In another aspect, this invention provides an injection device comprising an elongate housing for receiving in use a syringe or cartridge, the housing having a forward end and a rearward end, and the syringe or cartridge having a needle which projects from the forward end of said assembly at least on completion of an injection process, the needle being initially protected by a longitudinally removable sheath, said device further including a removable cap for being fitted to the forward end of the housing, said cap having a rearwardly extending element adapted to engage at its rearward end behind a base of the removable sheath, whereby upon removal of said cap from the forward end of said housing, said sheath is pulled off said needle.

Whilst the invention has been described above, it extends to any inventive combination of the features set out above or in the following description or claims.

BRIEF DESCRIPTION OF THE DRAWINGS

The invention may be performed in various ways, and in an embodiment thereof will now be described by way of example only, reference being made to the accompanying drawings in which:

FIG. 1 is a side view of an injection device in accordance with this invention prior to injection, with the shutter in its concealing position;

FIG. 2 is a section view through the device of FIG. 1;

FIG. 3 is a side view of the injection device of FIG. 1 but with the shutter retracted to its revealing position;

FIG. 4 is a cross-sectional view of the arrangement of FIG. 3;

FIG. 6 is a cross-sectional view through the injection device of FIG. 1 following injection, with the needle exposed, and FIG. 7 is a side view of the injection device following injection but with the cap refitted.

Figure 5:
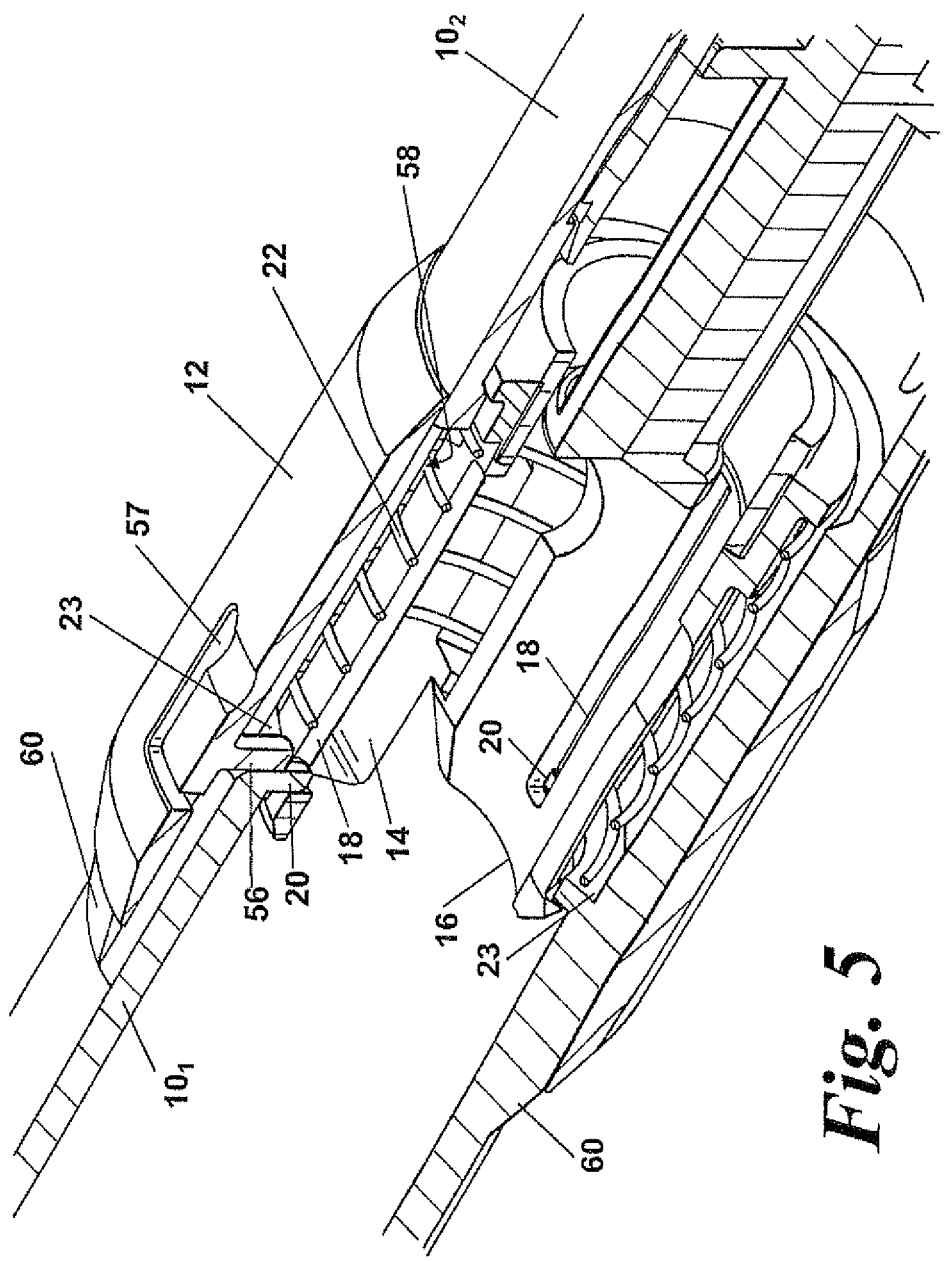
FIG. 5 is a detailed perspective cutaway view of the shutter element and the syringe carrier in the arrangement of FIG. 1, but with the syringe removed for clarity.

The injection device shown in the drawings is intended to be a single use device for administering therapeutic materials such as, for example, adrenalin in the case of anaphylactic shock. The device comprises a generally cylindrical housing 10 made up of a forward section $10_1$, a mid section $10_2$, a rear section $10_3$ and a rear collar $10_4$. Slideably mounted around the outside of the mid-section $10_2$ is a shutter element 12 which is moveable between a forward, concealing position shown in FIGS. 1 and 2, and a rearward, revealing position as shown in FIGS. 3 and 4, in which a window 14 provided on the side of the central section $10_2$ is revealed, and through which the contents of a syringe 25 can be viewed.

Referring specifically to FIGS. 2, 4, 5 and 6, a syringe carrier 16 is slideably mounted within the housing central section $10_2$ between a rearward position shown in FIGS. 2 and 4, and a forward position shown in FIG. 6. Referring to FIG. 5, the syringe carrier 16 is also of generally cylindrical form and is provided with two diametrically opposed slots 18 which receive two radially inwardly projecting abutments 20 on the central section $10_2$ to constrain longitudinal movement of the syringe carrier 16. The syringe carrier 16 is biased rearwardly by a compression coil spring 22 which contacts at its forward end a rear-facing shoulder 23 forming part of the central section $10_2$. The syringe carrier receives a syringe 24 comprising a glass or other transparent capsule, with a needle 26 at its forward end and a slideable bung 28 for expelling the material in the syringe. The needle 26 is initially shrouded by a needle sheath 30 which is a push fit over the needle spigot 32.

DESCRIPTION OF PREFERRED EMBODIMENTS

A needle cap 34 comprises an outer collar 36 and a rearwardly extending cylindrical open-ended portion 38 which has at its rearward end an inwardly directed rib 40 which sits in the gap between the rear end of the needle sheath 30 and the forward shoulder of the syringe 24. The rearward face of the rib 40 is bevelled such that, during assembly, can be pushed over the needle cap 30 to snap into the gap between the cap and the syringe shoulder.

At the rearward end of the injection device there is a provided a spring-loaded plunger 42 which has a forward end 44 dimensioned to fit within the syringe envelope contact the bung 28 and a forward flange 46 adapted in use to contact the rear end of the syringe 24 to limit the forward driving movement applied to the bung 28. A compression drive spring 48 acts between a rearward flange 50 of the plunger and an inner surface of the rear housing collar 104. The plunger has a split arrowhead 50 configuration of known form which releasably engages a retention surface 52 on the rear housing collar 104.

A safety button 54 fits in a slot in the split arrowhead 50 to prevent inadvertent firing. Upon removal of the safety cap 54, a firing button 56 is exposed which, when depressed, squeezes the split arrowhead to release it from engagement.

The shutter element 12 is provided with two inwardly directed resilient struts 56 which project through respective slots 58 provided in the central portion $10_2$ of the housing to limit longitudinal movement of the shutter element 12. The struts 56 engage the forward end of the compression spring 22 which also biases the syringe carrier 16 rearwardly. The struts 56 are made resilient by forming the collar 12 with two U-shaped cut-outs 57. The forward end of the central section $10_2$ is chamfered as shown at 60 so that the shutter 12 may be assembled by sliding over the forward end of the housing so that the struts 56 are temporarily displaced outwards by the chamfer 60 then to drop into the forward end of the slots 58 to engage the spring 22. Prior to use, before the injection, the shutter element 12 may be pulled back against the bias provided by the compression spring 22 to reveal the window 14 for inspection of the contents of the syringe.

In use, the needle cap 34 is removed by pulling it off forwardly and, as this is done, the rib 40 pulls the needle sheath 30 off the needle. The user then places the forward end of the housing against the intended injection site, removes the safety cap 54 and presses the firing button 56. This squeezes the arrowheads 50 together, thus releasing the plunger so that it is driven forwardly by the drive spring 48 initially to move the syringe forwardly with the syringe carrier 16, due to the friction between the bung 28 and the syringe capsule and also to the generally incompressible nature of the fluid contents of the capsule. This forward movement continues until the rear end of the slot 18 contacts the inwardly directed pin 20 on the housing, whereafter the plunger drives bung 28 forwardly to expel the dose until the flange 46 engages the rear end of the syringe. The user then removes the injection device from the injection site, at which point it is in the state shown in FIG. 6, with the needle projecting. The user then inverts the needle cap 34 so that the outer collar fits over and around the forward end of the housing 10 with the cylindrical portion 38 shielding the needle. This action may be a one way snap-fit.

This feature of a reversible cap provides multiple functionality; it closes and seals the housing prior to use; it locates the forward end of the syringe against lateral movement; it allows easy removal of the needle sheath, and provides a simple yet effective needle shroud to render the device safe after use.

Following injection, with the device in the state shown in FIG. 6, the syringe carrier is held at its forward limit of movement because the force of the drive spring is much stronger than that of the compression spring 22. Thus the forward position of the syringe carrier prevents a constraining movement of the shutter element 12, and this provides an external indication that the device has been used.

The invention claimed is:

1. An injection device comprising:
    an elongate housing for receiving a syringe or capsule, the housing having a window or viewing aperture through which contents of the syringe or capsule are selectably inspected before a delivery of a dose from the syringe or capsule;
    a shutter element movable between a revealing position in which said window or viewing aperture is visible and a concealing position in which said window or viewing aperture is concealed, and
    a bias element placing said shutter element in its concealing position,
    wherein when the syringe or capsule has been loaded into the injection device and prior to the delivery of the dose from the syringe or capsule, said shutter element is selectably retractable to the revealing position against an urging of the bias element to enable inspection of the contents of the syringe or capsule, and on release of the shutter element from its revealing position the bias element urges the shutter element to return to its concealing position.

2. An injection device according to claim 1, wherein said shutter element comprises a sleeve element generally surrounding said housing and slideable with respect thereto.

3. An injection device according to claim 2, wherein said bias element comprises a spring.

4. An injection device according to claim 1, wherein said bias element comprises a spring.

5. An injection device according to claim 4, wherein said spring comprises a coil spring arranged generally concentrically within said housing.

6. An injection device according to claim 5, wherein said shutter element is movable generally longitudinally with respect to said housing and said housing comprises at least one elongate slot adjacent said coil spring, and said shutter element includes an inwardly projecting portion adapted to protrude inwardly through said slot to engage said spring.

7. An injection device according to claim 6, wherein said housing includes slots disposed one in each side of the housing, and said shutter element includes respective projecting portions.

8. An injection device according to claim 6, wherein the or each inwardly projecting portion is resiliently flexible.

9. An injection device according to claim 1, wherein said housing includes a carrier for receiving in use said syringe or capsule, said carrier being mounted for generally longitudinal movement between a forward and a rearward position.

10. An injection device according to claim 9, wherein said bias element also biases said carrier.

11. An injection device according to claim 9, wherein said carrier includes an elongate slot and an inward projection on the housing cooperates with said slot to limit longitudinal movement.

12. An injection device according to claim 1, wherein said bias element comprises a spring and said shutter element is movable generally longitudinally with respect to said housing,
said housing comprising at least one elongate slot adjacent to said spring,
said shutter element comprising an upwardly projecting portion adapted to protrude inwardly through said at least one elongate slot to engage said spring,
said housing further comprising a carrier for receiving said syringe or capsule, said carrier being mounted for generally longitudinal movement between a forward and a rearward position,
said carrier comprising a further elongate slot, wherein said housing has an inward projection cooperating with said further elongate slot on said carrier to limit longitudinal movement of said carrier,
wherein the at least one elongate slot on the housing is generally aligned with the further elongate slot on the syringe carrier, and the inward projection on the housing is disposed on one end of the at least one elongate slot on the housing.

13. An injection device comprising:
an elongate housing for receiving a syringe or capsule, the housing having a window or viewing aperture through which contents of the syringe or capsule are selectably inspected before a delivery of a dose from the syringe or capsule;
a shutter element movable longitudinally between a revealing position in which said window or viewing aperture is visible and a concealing position in which said window or viewing aperture is concealed; and
a bias element urging said shutter element from the revealing position to the concealing position, said shutter element being selectively movable to the revealing position from the concealing position against the urging of the bias element,
wherein when the syringe or capsule has been loaded into the injection device and prior to the delivery of the dose from the syringe or capsule, said shutter element is selectably retractable to the revealing position against an urging of the bias element to enable inspection of the contents of the syringe or capsule, and on release of the shutter element from its revealing position the bias element urges the shutter element to return to its concealing position.

14. An injection device comprising:
a syringe in an elongate housing, the syringe having a needle enclosed within the housing, the housing having a viewing aperture through which contents of the syringe are selectably inspected before a delivery of a dose from the syringe;
a shutter movable longitudinally between a revealing position in which said viewing aperture is visible and a concealing position in which said viewing aperture is concealed; and
a bias element urging said shutter element to move from the revealing position to the concealing position,
wherein when the syringe has been loaded into the injection device while the needle is enclosed within the housing and prior to the delivery of the dose from the syringe, said shutter is selectably retractable to the revealing position against an urging of the bias element to enable inspection of the contents of the syringe, and on release of the shutter element from its revealing position the bias element urges the shutter element to return to its concealing position.

\* \* \* \* \*